(12) United States Patent
Gramatikov et al.

(10) Patent No.: US 8,678,592 B2
(45) Date of Patent: Mar. 25, 2014

(54) METHOD AND APPARATUS FOR DETECTING FIXATION OF AT LEAST ONE EYE OF A SUBJECT ON A TARGET

(75) Inventors: Boris I. Gramatikov, Baltimore, MD (US); David L. Guyton, Baltimore, MD (US); Kristina Irsch, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 14 days.

(21) Appl. No.: 13/416,979

(22) Filed: Mar. 9, 2012

(65) Prior Publication Data

US 2012/0229768 A1 Sep. 13, 2012

Related U.S. Application Data

(60) Provisional application No. 61/450,996, filed on Mar. 9, 2011.

(51) Int. Cl.
*A61B 3/10* (2006.01)

(52) U.S. Cl.
USPC ....................................................... 351/215

(58) Field of Classification Search
USPC ....................................................... 351/215
See application file for complete search history.

(56) References Cited

U.S. PATENT DOCUMENTS

| 6,027,216 | A | 2/2000 | Guyton et al. | |
| 2009/0244485 | A1* | 10/2009 | Walsh et al. | 351/221 |
| 2009/0316111 | A1* | 12/2009 | Hunter et al. | 351/201 |
| 2010/0253908 | A1* | 10/2010 | Hammer et al. | 351/206 |

OTHER PUBLICATIONS

Akaike, Hirotugu, A New Loot at the Statistical Model Identification, IEEE Transactions on Automatic Control, vol. 19, No. 6, Dec. 1974, pp. 716-723.
Bastiaans, Martin J., Gabor's Expansion of a Signal Into Gaussian Elementary Signals, Proceedings of the IEEE, vol. 68, No. 4, Apr. 1986, pp. 538-539.
Bastiaans, Martin J., A sampling theorem for the complex spectrogram and Gabor's expansion of a signal in Gaussian elementary signals, Optical Engineering, vol. 20, No. 4, Jul./Aug. 1981. pp. 594-598.
Classen, T.A.C.M. et al., The Wigner Distribution—A Tool for Time-Frequency Signal Analysis, Phillips Journal of Research, vol. 35, Nos. 4/5, 1980, pp. 276-300.
Cohen, Leon, Wigner Distribution for Finite Duration or Band-Limited Signals and Limiting Cases, IEEE Transactions on Acoustics, Speech, and Signal Proceeding, vol. ASSP-35, No. 6, Jun. 1987, pp. 796-806.

(Continued)

*Primary Examiner* — Scott J Sugarman
*Assistant Examiner* — Mustak Choudhury
(74) *Attorney, Agent, or Firm* — Venable LLP; Henry J. Daley (57) ABSTRACT

An apparatus for detecting fixation of at least one eye of a subject on a target includes an optical illumination system, an optical detection system, and a signal processing system adapted to communicate with the optical detection system. The signal processing system is configured to calculate at least one of a time-frequency distribution or an Auto-Regressive spectral estimation of the detection signal to provide a frequency distribution of the detection signal at a plurality of times for use in determining periods in which the subject's eye is fixed on the target based on the first and second frequency signatures.

14 Claims, 7 Drawing Sheets

(56) References Cited

OTHER PUBLICATIONS

Gramatikov, Boris, et al., Wavelet Analysis of Coronary Artery Occulsion Related Changes in ECG, IEEE 1983, p. 731.

Gramatikov, B. et al., Wavelets as alternative to short-time Fourier transform in signal-averaged electrocardiograpy, Medical & Biological Engineering & Computing, 33, May 1995, pp. 482-487.

Gramatikov, Boris, et al., Wavelet analysis and time-frequency distributions of the body surface ECG before and after angioplasty, Computer Methods and Programs in Biomedicine 62 (2000), pp. 87-98.

Hinich, Melvin J., Testing for Dependence in the Input to a Linear Time Series Model, Nanoparametic Statistics, vol. 6, 1996, pp. 205-221.

Hunter, David G., et al., Automated detection of foveal fixation by use of retinal birefringence scanning, Applied Optics, vol. 38, No. 7, Mar. 1999, pp. 1273-1279.

David G. Hunter, et al., Pediatric Vision Screener 1: instrument design and operation, Journal of Biomedical Optics, vol. 9, No. 6, Nov./Dec. 2004, pp. 1363-1368.

lrsch, K., et al. Spinning wave plate design for retinal birefringence scanning, Proc. of SPIE, vol. 7169. 2009, pp. 1-12.

Kay, Steven M., et al., Spectrum Analysis—A Modern Perspective, Proceedings of the IEEE, vol. 69, No. 11, Nov. 1981, pp. 1380-1419.

Kronland-Martinet, et al., Analysis of Sound Patterns Through Wavelet Transforms, International Journal of Pattern Recognition and Artificial Intelligence, vol. 1, No. 2, 1987, pp. 273-302.

Nassif, Deborah, et al., Pediatric Vision Screening using Binocular Retinal Birefringence Scanning, Proceedings of SPIE, vol. 4951, 2003, pp. 9-20.

Nikias, Chrysostomos L., Bispectrum Estimation: A Digital Signal Processing Framework, Proceedings of the IEEE, vol. 75, No. 7, Jul. 1987, pp. 869-891.

Olivier, Rioul, et al., Wavelets and Signal Processing, IEEE SP Magazine, Oct. 1991, pp. 14-38.

* cited by examiner

METHOD AND APPARATUS FOR DETECTING FIXATION OF AT LEAST ONE EYE OF A SUBJECT ON A TARGET

CROSS-REFERENCE OF RELATED APPLICATION

This application claims priority to U.S. Provisional Application No. 61/450,996 filed Mar. 9, 2011, the entire contents of which are hereby incorporated by reference.

BACKGROUND

1. Field of Invention

The field of the currently claimed embodiments of this invention relates to apparatuses and methods for detecting fixation of at least one eye of a subject on a target.

2. Discussion of Related Art

In recent years, the birefringent properties of the Henle fibers surrounding the fovea of a person's eye have been used to identify the position of the fovea and the direction of gaze. This allows for one to check for eye alignment and strabismus, a risk factor for amblyopia. Screening techniques have been reported that are based on the birefringence signal derived from foveal circular scanning. In this approach, a signal s(t) consisting of several frequency components ($f_1=k_1*f_s$, $f_2=k_2*f_s$, $f_3=k_3*f_s$, etc.) is produced, where each frequency is a multiple or multiple of a fraction of the scanning frequency $f_s$. Some frequencies prevail during central fixation, while others appear at para-central fixation. The existence and the mixture of frequencies depend on the opto-mechanical design. In the simplest case, $f_2=2f_s$ is produced during central fixation, while $f_1=f_s$ prevails during off-central fixation. Existing instruments acquire consecutive epochs of s(t), with gaps between them, during which an (Fast Fourier Transform) FFT is performed. (See, for example, U.S. Pat. No. 6,027,216, the entire contents of which are hereby incorporated herein by reference.) A problem with this approach is that the FFT power spectrum is a global measure, i.e., it provides information on how much of $f_1$ and $f_2$ are represented in the whole epoch analyzed, but it does not provide information on exactly where these frequencies appear and for how long. With less-cooperative patients, important short lasting moments of central fixation ($f_2$) may easily be hidden behind large low-frequency ($f_1$) components. Analyzing short time intervals is desirable, but this is where the FFT becomes prone to noise and loses spectral resolution. There thus remains a need for improved apparatuses for detecting fixation of at least one eye of a subject on a target.

SUMMARY

An apparatus for detecting fixation of at least one eye of a subject on a target according to an embodiment of the current invention includes an optical illumination system arranged to scan at least a portion of the retina of an eye of the subject with an illuminating beam of light, an optical detection system arranged to detect at least a portion of the illuminating beam of light after being reflected back from the retina of the subject's eye to provide a detection signal, and a signal processing system adapted to communicate with the optical detection system to receive the detection signal. The illuminating beam of light is polarized light such that reflected portions of the illuminating beam are affected by birefringence of substructures of the retina of the subject's eye. The detection signal has a first frequency signature when the subject's eye is fixed on the target and a second frequency signature when the subject's eye is not fixed on the target. The signal processing system is configured to calculate at least one of a time-frequency distribution or an Auto-Regressive spectral estimation of the detection signal to provide a frequency distribution of the detection signal at a plurality of times for use in determining periods in which the subject's eye is fixed on the target based on the first and second frequency signatures.

A method for detecting fixation of at least one eye of a subject on a target according to an embodiment of the current invention includes scanning at least a portion of the retina of an eye of the subject with an illuminating beam of light, detecting at least a portion of the illuminating beam of light after being reflected back from the retina of the subject's eye to provide a detection signal, and processing the detection signal. The illuminating beam of light is polarized light such that reflected portions of the illuminating beam are affected by birefringence of substructures of the retina of the subject's eye. The detection signal has a first frequency signature when the subject's eye is fixed on the target and a second frequency signature when the subject's eye is not fixed on the target. The processing of the detection signal includes calculating at least one of a time-frequency distribution or an Auto-Regressive spectral estimation of the detection signal to provide a frequency distribution of the detection signal at a plurality of times for use in determining periods in which the subject's eye is fixed on the target based on the first and second frequency signatures.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The term "light" as used herein is intended to have a broad meaning that can include both visible and non-visible regions of the electromagnetic spectrum. For example, visible, near infrared, infrared and ultraviolet light are all considered as being within the broad definition of the term "light."

Figure 1:
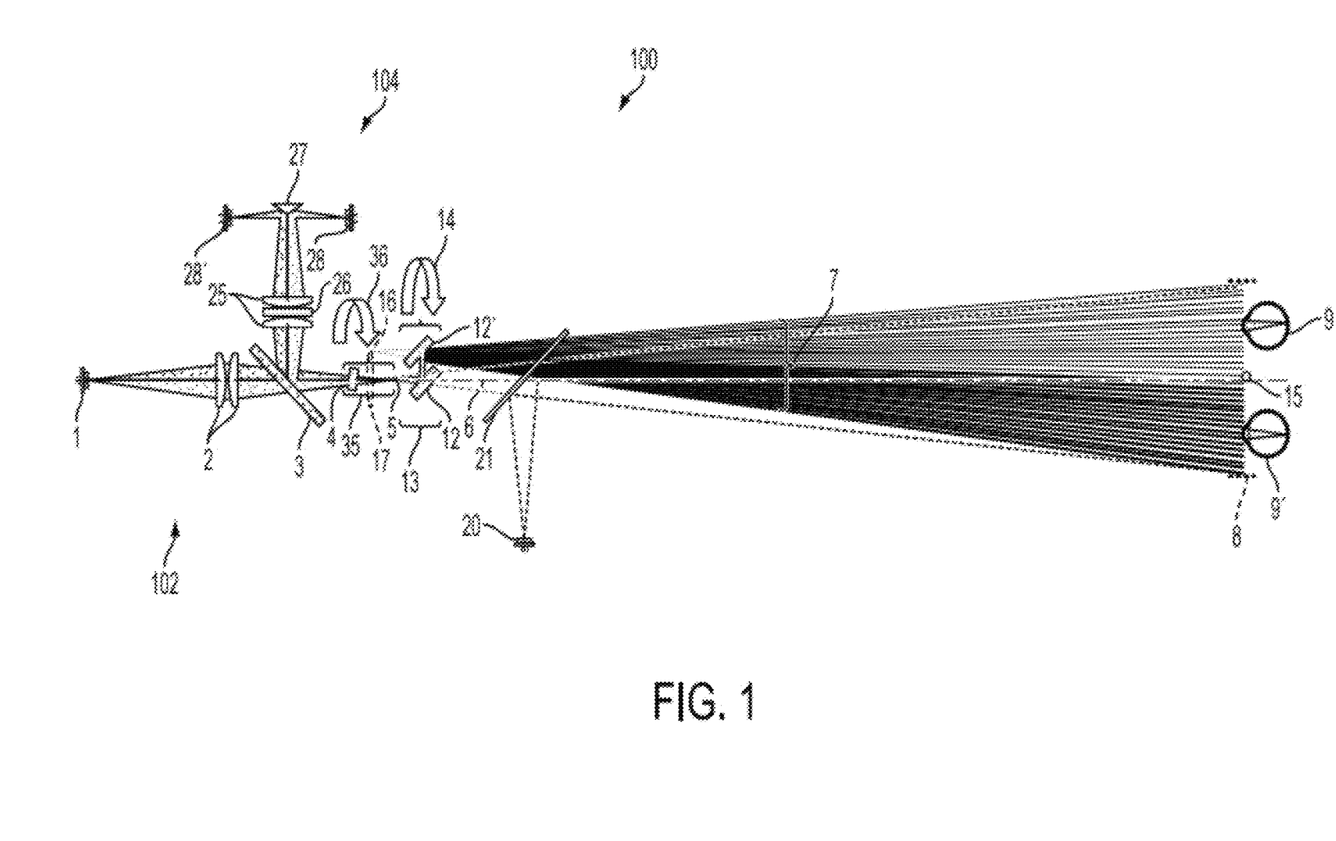
FIG. 1 is a schematic illustration of optical, mechanical and sensor components of an apparatus for detecting fixation of at least one eye of a subject on a target according to an embodiment of the current invention.

FIG. 1 provides a schematic illustration of an apparatus 100 for detecting fixation of at least one eye of a subject on a target according to an embodiment of the current invention. The apparatus 100 includes an optical illumination system 102 arranged to scan at least a portion of the retina of an eye of the subject with an illuminating beam of light, an optical detection system 104 arranged to detect at least a portion of the illuminating beam of light after being reflected back from the retina of the subject's eye to provide a detection signal, and a signal processing system (not shown in FIG. 1) adapted to communicate with the optical detection system to receive the detection signal. The illuminating beam of light is polarized light such that reflected portions of the illuminating beam are affected by birefringence of substructures of the retina of the subject's eye. The detection signal has a first frequency signature when the subject's eye is fixed on the target and a second frequency signature when the subject's eye is not fixed on the target. The signal processing system is configured to calculate at least one of a time-frequency distribution or an Auto-Regressive spectral estimation of the detection signal to provide a frequency distribution of the detection signal at a plurality of times for use in determining periods in which the subject's eye is fixed on the target based on the first and second frequency signatures.

The term "reflected" is intended to have a broad meaning and is not limited to only specular reflection. For example, light scattered back from an optically rough, or semi-rough surface is intended to be included within the definition of the term "reflected."

The term "frequency signature" is intended to include a signal that has one or more frequency components which can be identified with preselected one or more frequency components. The first frequency signature is distinguishable from the second frequency signature. In some cases, the first and second frequency signatures can each be one dominating frequency component, but at different frequencies. However, each of the first and second frequency signatures can have one, two, three or more frequency components. These signatures can be thought of as identifying a two-state system, i.e., the eye is fixed on the target (central fixation) or not fixed on the target. In the case in which the eye is not fixed on the target, it may be off-central fixation, for example. These two states of fixation may be considered central fixation and non-central fixation, for example.

The substructures of the portion of the retina of the subject's eye scanned can include Henle fibers surrounding a fovea of the subject's eye.

In some embodiments, a time resolution of the at least one of a time-frequency distribution or an Auto-Regressive spectral estimation is smaller than 0.2 seconds and a frequency resolution of the time-frequency distribution is smaller than 50 Hz. In some embodiments, the time resolution of the at least one of a time-frequency distribution or an Auto-Regressive spectral estimation is smaller than 0.03 seconds and the frequency resolution of the time-frequency distribution is smaller than 5 Hz. In some embodiments, the time resolution of the at least one of the time-frequency distribution or the Auto-Regressive spectral estimation is sufficient to provide the frequency distribution that resolves frequency components of the frequency signatures for time intervals shorter than an average involuntary reflex time of human subjects.

In some embodiments, the signal processing system is configured to calculate the time-frequency distribution using at least one of a short time Fourier transform, a Continuous Wavelet Transform, a Wigner-Ville distribution, a Gabor Transform, or a Choi-Williams distribution.

In some embodiments, the signal processing system is configured to calculate the Auto-Regressive spectral estimation employing at least one of a Yule-Walker, Burg, Covariance, Modified covariance, Marple, least-square (LS) method, a Levinson-Durbin algorithm, a maximum likelihood estimation (MLE) method, Maximum Entropy (ME) method, or Prony method.

In some embodiments, the optical illumination system can include a scanning assembly configured to scan the illuminating beam in a cyclical spatial pattern on the portion of the retina at a scanning frequency. The cyclical spatial pattern can be circular, but it is not limited to only circular scans. For example, elliptical scans are also included within the general definition of the term "cyclical spatial pattern." However, the broad concepts of the current invention are not limited to these examples.

The first frequency signature can include at least one frequency component that is directly proportional to the scanning frequency by a first proportionality constant and the second frequency signature can include at least one frequency component that is directly proportional to the scanning frequency by a second proportionality constant such that the first proportionality constant has a different value from a value of the second proportionality constant.

In some embodiments, the optical illumination system can further include a polarization modulating assembly configured to modulate polarization of the illuminating beam at a polarization modulation frequency (See, for example, Irsch K. Polarization modulation using wave plates to enhance foveal fixation detection in retinal birefringence scanning for pediatric vision screening purposes. PhD thesis 2009. University of Heidelberg. URL: http://www.ub.uni-heidelberg.de/archiv/8938/; Irsch K, Gramatikov B I, Wu Y K, Guyton D L. Spinning wave plate design for retinal birefringence scanning. Proc of SPIE 2009; 7169:71691F1-12), the entire contents of which are incorporated herein by reference). The polarization modulation frequency can be selected relative to the scanning frequency to provide at least partial cancellation of optical noise in the optical detection system.

In some embodiments, the optical illumination system can be further adapted to scan at least a portion of a retina of the second eye of the subject with a second illuminating beam of light to operate as a binocular system. In some embodiments, the second scanning and detection system can be structured and operate as the above-noted system. Information from both eyes taken at the same time (or at least at time intervals that are short compared to average reflex time periods for subjects) can provide additional relative information regarding the state of fixation of both eyes together, for example.

In some embodiments, the optical detection system can further include a bull's eye photodetector that has concentric central and annular sensors to detect a focus quality of the light after being reflected back from the retina of the subject's eye.

The following will now describe the embodiment of FIG. 1 in more detail. The broad concepts of the current invention are not limited to this particular embodiment. In FIG. 1, laser diode 1 provides a substantially point source of near infrared light that is linearly polarized vertically. This light is imaged by lenses 2 through polarizing beam splitter 3 and spinning half wave plate 4 to aerial point image 5 on optical axis 6, wherefrom the light diverges in light beam 7 to fill stationary exit pupil 8 located substantially at the pupillary planes of right eye 9 and left eye 9' of a test subject. The plane containing eyes 9 and 9' is rotated 90 degrees about optical axis 6 to facilitate the description. Right eye 9 is normally behind the plane of the Figure and left eye 9' is in front. Flat mirrors 12 and 12' are rigidly fixed in scanning assembly 13 which is continuously rotated according to arrow 14 about optical axis 6 by mechanical components not shown. As scanning assembly 13 rotates about optical axis 6, light beam 7 pivots about point 15 in the center of exit pupil 8. In the momentary position of light beam 7 shown in FIG. 1, eyes 9 and 9' see the near infrared light as coming from virtual point image 16. As light beam 7 is scanned about by mirrors 12 and 12' in scanning assembly 13, eyes 9 and 9' see virtual image 16 scanned circularly, creating a circle of light, scanning circle 17.

Laser diode 20 provides a substantially point source of red light which diverges to be reflected by cold mirror 21 to fill exit pupil 8 at eyes 9 and 9'. This red light from laser diode 20 is blinking and synchronized with an audible sound effect to attract attention in some embodiments, and is provided for eyes 9 and 9' to fixate upon. Cold mirror 21 passes the near infrared light in light beam 7, which is seen by eyes 9 and 9' as a faint scanning circle of light. Eyes 9 and 9' see the blinking fixation point of red light as coming from the center of the faint scanning circle 17 of near infrared light. By fixating and focusing upon the central point of red light, the test subject also becomes focused on the plane containing scanning circle 17, establishing optical conjugacy between the point source of near infrared light from laser diode 1 and the retinas of eyes 9 and 9', such that scanning circle 17 is in focus on the retinas of eyes 9 and 9'.

The polarized near infrared light from light beam 7 that enters eyes 9 and 9' is partly reflected from the fundus of each of those eyes, double passing the transparent birefringent nerve fibers in the retina. The "form" birefringence of these nerve fibers changes the polarization state of the near infrared light. The type of change at each point in the scan is a function of the number and orientation of the nerve fibers at that point in the scan.

The near infrared light reflected from each fundus of eyes 9 and 9' is imaged back respectively by eyes 9 and 9', following the light path it originally came from, via the principle of conjugacy. The portion of this light that is still polarized vertically passes back through polarizing beam splitter 3 toward the original light source 1. The portion of this near infrared light that has been changed by the birefringence of the nerve fibers in the retina, however, is reflected upward by polarizing beam splitter 3, passing through lenses 25 and narrow-band filter 26 to be reflected by reflecting knife-edge prism 27 to photodetectors 28 and 28'. Lenses 25 also image point 15 in the center of exit pupil 8 onto the knife edge of reflecting knife edge prism 27 so that light returning from right eye 9 of the test subject is reflected to right eye photodetector 28, and light returning from left eye 9' of the test subject is reflected to left eye photodetector 28'. The vertical plane containing photodetectors 28 and 28' is rotated 90 degrees about the vertical axis to facilitate the description. Right eye photodetector 28 is normally in front of the plane of the Figure and left eye photodetector 28' is behind.

Figure 2A:
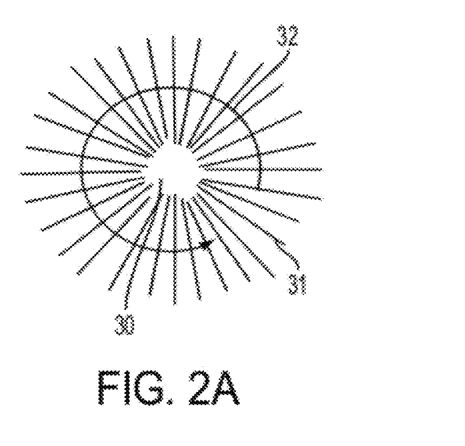
FIG. 2 is a schematic illustration of portions of a subject's eye to illustrate some concepts of the current invention.
Figure 2B:
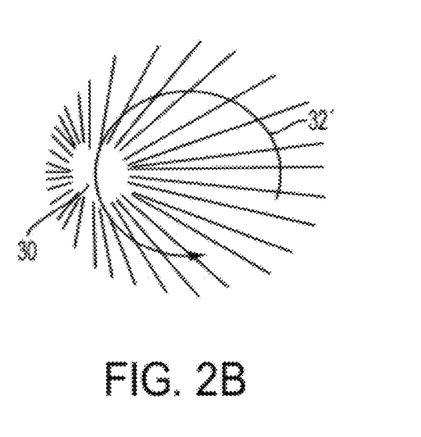

FIGS. 2A and 2B are diagrammatic representations of the fovea of a human eye, with the fovea being the portion of the retina with best visual acuity that is aimed at the object of fixation. Radiating outward from the center of the fovea 30 are birefringent nerve fibers termed Henle fibers 31, which are actually the elongated axons of the closely-packed photoreceptors in the fovea. In FIG. 2A, the image 32 of scanning circle 17 from FIG. 1 is centered on the fovea. Each orientation of Henle fiber is encountered twice in a single 360 degree scan, resulting in changes in the polarization state of the back-reflected light that have a frequency component of twice the scan frequency. In FIG. 2B, the image 32' of scanning circle 17 from FIG. 1 is decentered from the fovea. In this case, each orientation of Henle fiber is encountered only once during a single 360 degree scan, resulting in changes in the polarization state of the back-reflected light that have a predominant frequency component equal to the scan frequency. With continuous cycles of the circular scan, periodic signals are obtained from photodetectors 28 and 28' (in FIG. 1) for both eyes simultaneously. Analysis of the frequency components contained in these periodic signals can thus determine whether each eye is fixated on the red fixation light in the center of the circular scan, and if both eyes are fixating centrally simultaneously, binocular alignment of the eyes is confirmed. Any condition other than confirmed binocular alignment is reason for referral for further examination of the subject's eyes for the presence of strabismus, amblyopia, or other abnormal eye condition such as cataract or retinal disease.

Conventional algorithms for detection of fixation, as just described, can be found in the following, each of which is incorporated herein by reference:
1) Guyton D L, Hunter D G, Sandruck J C, Patel S N, Fry R L. Eye fixation monitor and tracker. U.S. Pat. No. 6,027,216, Feb. 22, 2000.
2) Hunter D G, Patel S N, Guyton D L. Automated detection of foveal fixation by use of retinal birefringence scanning. *Applied Optics* 1999; 38:1273-1279.
3) Nassif D S, Guyton D L, Gramatikov B, Hunter D G. Pediatric vision screening using binocular retinal birefringence scanning. In Manns F, Soederberg P G, Ho A, eds: *Proceedings of SPIE*, Vol. 4951: *Ophthalmic Technologies XIII. SPIE*, Bellingham, Wash., 2003, pp 9-20.
4) Hunter D G, Nassif, D S, Piskun N V, Winsor R, Gramatikov, B I, Guyton D L. The Pediatric Vision Screener. I. Instrument design and operation. J Biomed Optics 2004; 9:1363-1368.

In FIG. 1, the addition of spinning half wave plate 4 represents an improvement to the representative apparatus and detection algorithm just described. Half wave plate 4 is tilted to avoid back reflections and is rigidly fixed within spinning assembly 35 which is continuously rotated, according to arrow 36, about optical axis 6, by mechanical components not shown. The spinning frequency of the half wave plate can be a fraction of the scanning frequency of scanning assembly 13, a fraction such as 9/16 of the scanning frequency. The spinning half wave plate continuously rotates the axis of polarization of the linearly polarized light passing through it, twice as fast as the half wave plate rotates. As elaborated in Irsch K, Gramatikov B I, Wu Y K, Guyton D L. Spinning wave plate design for retinal birefringence scanning. *Proc of SPIE* 2009; 7169:71691F1-12 (the entire content of which is hereby incorporated by reference), the net effect of adding the spinning half wave plate is generation of frequency components for the centered and decentered conditions that are multiples of half of the scanning frequency. By shifting the resulting periodic signal by one scanning period and subtracting it from itself ("phase-shift subtraction"), the desired frequency components that are multiples of half the scanning frequency double in amplitude, and the frequency components that are whole multiples of the scanning frequency subtract out, significantly reducing optical noise within the instrument.

Analysis of the frequency components contained within the periodic signals from retinal birefringence scanning has heretofore relied upon the fast Fourier transform technique. Typically recording epochs of 10 to 30 scans (0.3 to 1.0 second recordings) are needed to provide enough temporal and spectral resolution for proper analysis with the Fast Fourier transform technique, mainly due to insufficient patient cooperation. Methods of analysis according to some embodiments of the current invention can provide better and faster temporal and spectral detection of the frequency components in the periodic signals from retinal birefringence scanning.

Electronics

Figure 3:
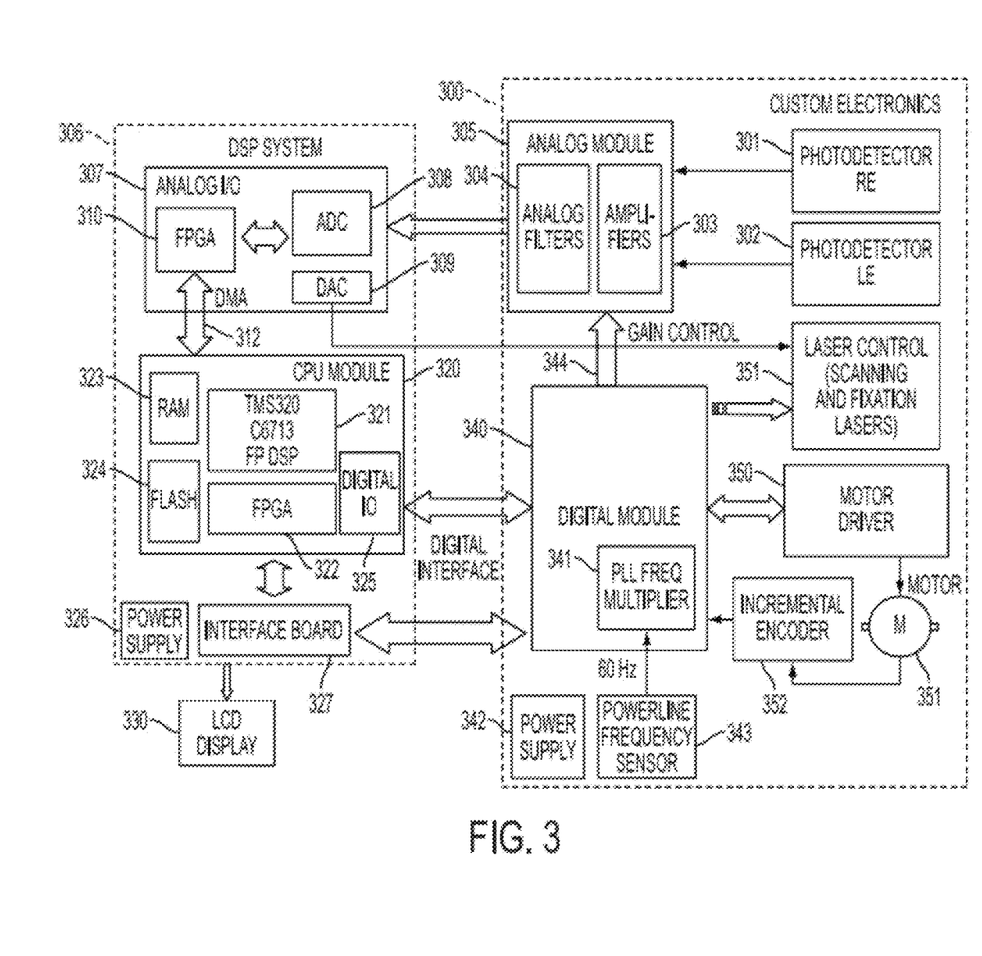
FIG. 3 is a schematic illustration of electronics components of an apparatus for detecting fixation of at least one eye of a subject on a target according to an embodiment of the current invention.

A simplified block diagram of the electronics according to an embodiment of the current invention is shown in FIG. 3. Signals from the photodetectors 301 and 302 are connected to the analog module 305 on a custom electronics board 300. The analog module contains amplifiers of controllable gain 303, and analog filters 304. From there they are fed to a 32-bit Digital Signal Processing (DSP) system 306 consisting of an analog input/output module 307, a central processing unit (CPU) module 320, an interface board 327, and power supply 326. The analog input/output module 307 further contains an analog-to-digital converter 308, a digital-to-analog converter 309, a field programmable gate array (FPGA) 310, and direct memory access hardware 312. The CPU module 320 contains the DSP chip 321, FLASH memory 324, RAM memory 323, a second FPGA device 322 accommodating reconfigurable digital logic, and traditional digital I/O logic 325 such as parallel interface, serial interface etc.

In addition to the analog module 305, the custom electronic hardware 300 contains further a digital module 340. The digital module contains the control electronics, motor speed sensors, PLL frequency multiplier 341, interface to the CPU module 320, interface to the laser diode drivers 351, and interface to the step motor 351, which includes forward control over the motor driver 350, and feedback over the incremental encoder 352. The intensity of the scanning laser is controlled by software via a signal from the digital-to-analog converter 309. The custom electronics 300 is powered independently by a power supply 342. The system also contains a touch-screen LCD display 330 which serves as user interface.

Control of the Scanning Motor and Data Acquisition

The phase-shift subtraction method requires a very stable motor speed, as well as data sampling at precise moments in time corresponding to well-defined motor shaft angles during each scan. At each new step, one sample from each channel is acquired, i.e. every new data sample corresponds to a fixed angle of rotation (1 step). Each sample during one scanning rotation corresponds to one particular angle of rotation, with the angles spaced at precise intervals. This can be achieved by either using a DC motor with an incremental encoder that paces directly the ADC, or by using a step motor. In one embodiment, in order to eliminate also the powerline interference along with the instrumental noise in the phase-shift subtraction procedure, a step motor is paced with a frequency which is a precise multiple of the 60 Hz powerline frequency. The data epoch is a multiple of the powerline period (1/60 sec). With every data acquisition starting at a predefined phase of the scanning circle and of the powerline, there are a whole number of complete powerline cycles in one scanning cycle, which means that powerline noise is eliminated by the 360° phase-shift subtraction technique. Multiplication of the powerline frequency by a factor N is achieved by means of the phase-locked-loop (PLL) circuit 341. Synchronizing ADC with the power line and with the scanning system greatly reduces the noise and at the same time enables the phase-shift subtraction.

Time-Frequency Distributions

Some embodiments of the current invention provide improved methods of signal analysis for instruments that use a scanning spot of polarized light on the retina to determine whether or not the eye is fixating on a specified target. A circular scan of light can be used such that it spatially surrounds the specified target upon which fixation is expected. This can enable the acquisition of a birefringence-related signal from double passage through the birefringent nerve fibers encountered by the scanning spot of light. From analysis of the resulting birefringence-related signal, the state of fixation on the fixation target can be determined. Some conventional systems of this general type can be found in (Guyton, Hunter 2000), the entire contents of which are incorporated herein by reference. Those systems generally produce a periodic signal arising from polarization-related changes in the light retroreflected from the fundus of the eye, with dominating signal components of a certain frequency $f_1 = k_1 * f_s$ during lack of fixation, and of frequency $f_2 = k_2 *$ during fixation, where $f_s$ is the scanning frequency. The constants $k_1$ and $k_2$ can assume different values, depending on the optical design being used. Typically, the existing instruments analyze consecutive epochs of the birefringence-related signal s(t). The duration of the epoch, although directly proportional to the quality of the signal obtained, can become a limiting factor, especially when fast analysis is desired.

The existing instruments analyze consecutive sub-epochs of s(t), with gaps between them, during which a Fast Fourier Transform (FFT) is performed. A problem with this approach is that the FFT power spectrum is an "integral" approach, i.e., it tells us to what extent $f_1$ and $f_2$ are represented in the overall epoch analyzed, but it does not tell us exactly where these frequencies appear in that epoch and for how long. The conventional systems use FFT analysis. However, with pediatric patients, where subject cooperation is a problem, short lasting moments of central fixation ($f_2$) may easily be buried in the $f_1$ vs. $f_2$ relationship where non-central fixation often dominates. Moreover, in the gaps between the sub-epochs, where signal analysis takes place, valuable instants of central fixation may easily be missed.

For some applications, it is desirable to be capable of detecting short lasting moments of central fixation that are on the order of 10-30 ms in time domain and about 5 Hz in frequency domain.

A time-frequency distribution (TFD) of a signal provides information about how the spectral content of the signal evolves with time, thus providing a tool to dissect and interpret non-stationary signals. The need for a combined time-frequency representation stemmed from the inadequacy of either time domain or frequency domain analysis to fully describe the nature of non-stationary signals. TFD is performed by mapping a one dimensional signal in the time domain into a two dimensional time-frequency representation of the signal. In this approach, the photodetector signal s(t) is continuous and is analyzed continuously rather than fragmented into sub-epochs to be analyzed individually. However, it can be done, i.e., analyze while acquire (for which you need powerful hardware and a top-of the line firmware programmer), or acquire one long or very long time epoch, and then analyze it off-line.

Figure 4:
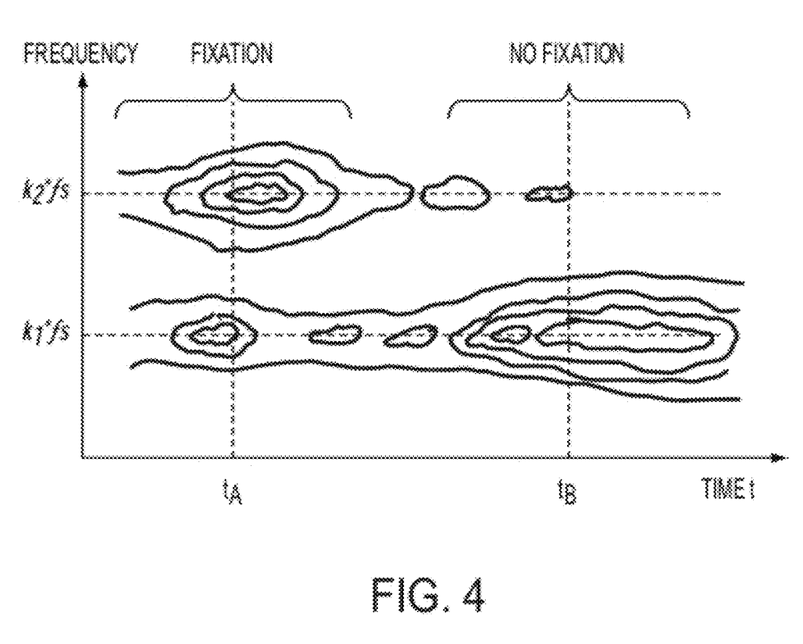
FIG. 4 is a schematic illustration of a Time-frequency distribution (TFD) of a retinal birefringence scanning (RBS) signal s(t) to help explain some concepts of an embodiment of the current invention. Note the existence of fixation frequency $k_2*f_s$ at moment $t_A$, and the absence of fixation at moment $t_B$ where $k_1*f_s$ is prevailing. Even though the two frequencies are not always strongly expressed due to possible artifacts, relatively simple TFD analysis can detect fixation reliably. This can make time-frequency distribution a powerful event detection tool in the case of an unstable signal in a noisy environment.

The center of the fovea is expected to be in the middle of the scanning circle during fixation. The sampling rate should be at least $2*k_2*f_s$ (scanning frequency) where $k_2$ is the largest proportionality constant of both frequency signatures. For every epoch (T=0.2 s to 3 s) of the incoming signal, a time-frequency distribution is being computed, as shown in FIG. 4. High-frequency (small scale) signal components can easily be distinguished from lower-frequency (larger scale) components, thus enabling detection of fixation on the target. Let us assume that the eye fixates on the target at moment $t_A$ and does not fixate at time moment $t_B$. Consequently, in the time-frequency plane (FIG. 4), we observe concentration of power at frequency $k_2*f_s$ at moment $t_A$, and then shift of the prevailing frequency to $k_1*f_s$ at moment $t_B$.

A variety of methods for obtaining the energy density of a function simultaneously in the time and frequency have been devised, most notably the short time Fourier transform (STFT), the Continuous Wavelet Transform (CWT), and the Wigner-Ville distribution (WVD). Time-frequency distributions can also be obtained using other, similar signal processing tools, such as the Gabor Transform (Bastiaans 1980, Bastiaans 1981, Qian and Chen 1996), the Choi-Williams distribution, and others.

The short-time. Fourier transform (also known as the windowed Fourier transform) localizes the signal by modulating it with a window function before performing the Fourier transform to obtain the frequency content of the signal in the region of the window. (Gramatikov and Georgiev 1995, Qian and Chen 1996) As a rule, it is a compromise between time and frequency resolution; the wider the window, the higher the frequency resolution, at the cost of poorer time resolution, and vice versa. Any attempt to increase the frequency resolution causes a larger window size and therefore a reduction in time resolution, and vice-versa. Also, in order to be able to analyze transients, overlapping windows need to be used, which can slow down analysis considerably.

The definition for the Wigner-Ville distribution used for time-frequency analysis is $$W_s(t, f) = \int_{-\infty}^{\infty} s\left(t + \frac{\tau}{2}\right) s^*(t - \tau/2) e^{-i2\pi\tau f} d\tau \quad (1)$$

where $i=\sqrt{-1}$ is the imaginary unit, and * denotes complex conjugation. (Claasen and Mecklenbrauker 1980, Cohen 1987, Qian and Chen 1996, Velez and Garudadri 1992) In essence, the WVD is the Fourier transform of the input signal's autocorrelation function, i.e. the Fourier spectrum of the product between the signal and its delayed, time reversed copy, as a function of the delay. Unlike the short-time Fourier transform, the Wigner distribution function is not a linear transform. A cross term ("time beats") occurs when there is more than one component in the input signal, analogous in time to frequency beats. In order to reduce the cross term problem, many other transforms have been proposed, including the modified Wigner distribution function, the Gabor-Wigner transform, Cohen's class distribution, and others.

Perhaps the best known member of Cohen's class distribution function is the Choi-Williams distribution function. (Qian and Chen 1996) This distribution function adopts an exponential kernel to suppress the cross-term.

$$C_g(t,f) = \int_{-\infty}^{\infty} \int_{-\infty}^{\infty} A_g(\eta,\tau) \Phi(\eta,\tau) e^{-i2\pi(\eta t - \tau f)} d\eta d\tau \quad (2)$$

where $$A_3(\eta, \tau) = \int_{-\infty}^{\infty} s\left(t + \frac{\tau}{2}\right) s^*(t - \tau/2) e^{-i2\pi\eta t} dt$$

and the kernel function is $$\Phi(\eta,\tau) = e^{-\alpha(\eta\tau)^2}.$$

However, the kernel gain does not decrease along the $\eta$ and $\tau$ axes in the ambiguity domain, and, consequently, the kernel function of the Choi-Williams distribution function can only filter out the cross-terms resulting from components away from the $\eta$ and $\tau$ axes and away from the origin.

The Continuous Wavelet Transform

A good method for obtaining time-frequency distributions is the Continuous Wavelet Transform (CWT) (Chui 1992, Claasen and Mecklenbrauker 1980, Debnath 2003, Gramatikov, Brinker 2000, Gramatikov and Georgiev 1995, Gramatikov and Thakor 1993, Hogan and Lakey 2005, Kronland-Martinet, Morlet 1987, Rioul and Vetterli 1991), which provides excellent localization of events in both time- and frequency domains. If the signal to be analyzed is $s(t)$, and $g(t)$ is the analyzing wavelet, the CWT is defined by:

$$W(\tau, a) = \frac{1}{\sqrt{a}} \int s(t) g^*\left(\frac{t-\tau}{a}\right) dt \quad (3)$$

where * denotes complex conjugation, a is the scale (dilation) with $a=1/f$, and $\tau$-a is the time shift. The wavelet $g(t)$ and the $W(\tau,a)$ are complex-valued in the general case. The constant $1/\sqrt{a}$ is used for energy normalization.

The analyzing wavelet $g(t)$ satisfies the following conditions: (Gramatikov and Georgiev 1995, Grossmann and Morlet 1984, Holschneider 1995, Kronland-Martinet, Morlet 1987)

(a) Belong to $L^2$ (R), i.e. be square integrable (be of finite energy);

(b) Be analytic ($G(\omega)=0$ for $\omega<0$) and thus be complex-valued.

(c) Be admissible. This condition was shown to enable invertibility of the transform:

$$s(t) = \frac{1}{c_g} \int_{-\infty}^{\infty} \int_{a>0}^{\infty} W(\tau, a) \frac{1}{\sqrt{a}} g\left(\frac{t-\tau}{a}\right) \frac{1}{a^2} da d\tau$$

where $c_g$ is a constant that depends only on $g(t)$ and a is positive. For an analytic wavelet this constant should be positive and convergent $$c_g = \int_0^{\infty} \frac{|G(\omega)|^2}{\omega} d\omega < \infty$$

which in turn imposes an admissibility condition on $g(t)$. For a real-valued wavelet, the integrals from both $-\infty$ to 0 and 0 to $+-\infty$ should exist and be greater than zero.

Admissible wavelets have no zero frequency contribution, or, what amounts to the $$\int_{-\infty}^{+\infty} g(t)\,dt = 0$$

same, they are of zero mean, or equivalently $G(\omega)=0$ for $\omega=0$:

An appropriate choice for an analyzing wavelet is the admissible complex-valued wavelets of Morlet (Kronland-Martinet, Morlet 1987) comprising a modulated window:

$$g_m(t) = e^{j\omega_0 t} e^{-\frac{t^2}{2}} \qquad (4)$$

Figure 5:
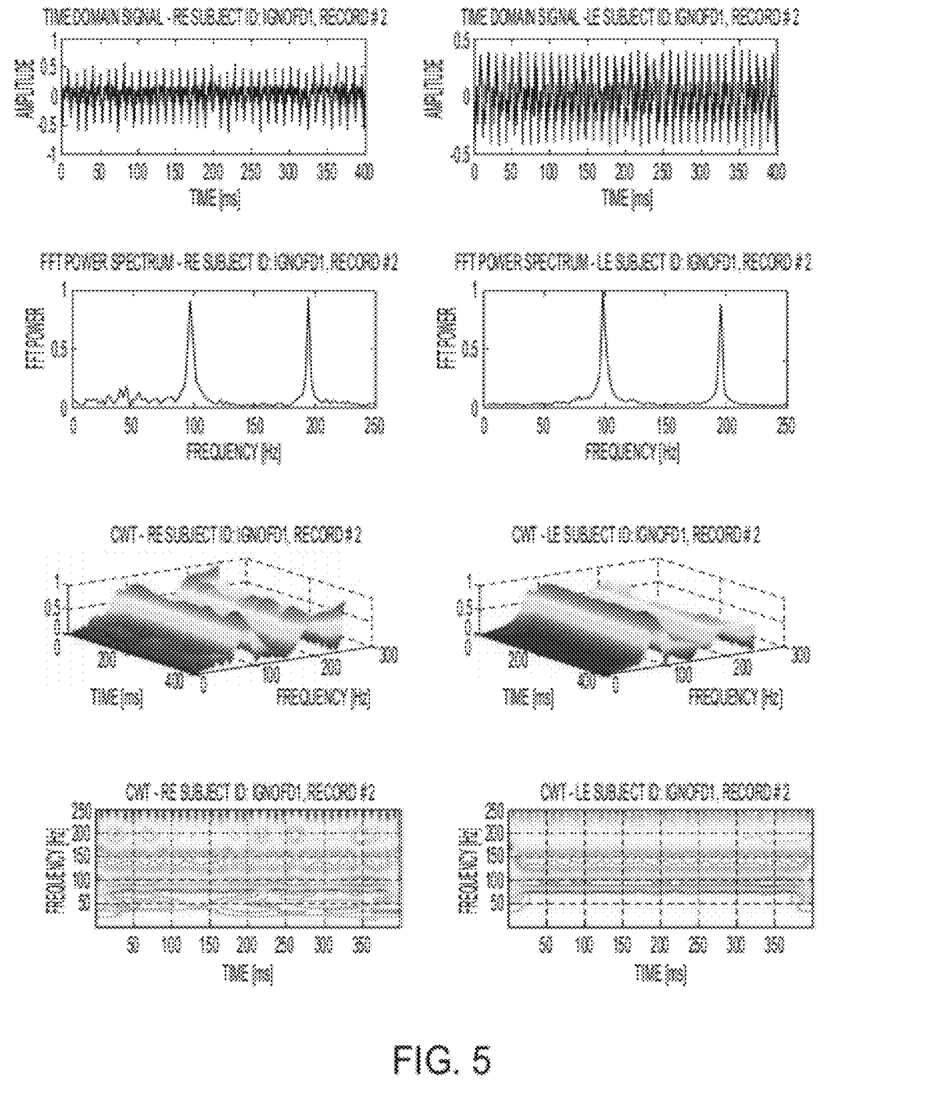
FIG. 5 shows real RBS signals taken from a 7-year old child with an instrument having a scanning frequency $f_s=96$ Hz, and $k_1=1$ (para-central fixation), $k_2=2$ (central fixation) to contrast an embodiment of the current invention with a conventional approach.

FIG. 5 shows real signals taken from a 7-year old child with an instrument having a scanning frequency $f_s=96$ Hz, and $k_1=1$ (para-central fixation), $k_2=2$ (central fixation). The left column represents the right eye (RE), while the right column represents the left eye (LE). The upper two graphs show the time domain scan signal s(t) for RE and LE, record #2 of 12. The second row presents the FFT power of the corresponding time signals. The FFT does detect the two frequencies ($f_1=96$ Hz and $f_2=192$ Hz), but cannot tell where in time they appear and for how long. The third and the forth rows show the CWT of the same signal as 3D plots and contour plots. Here episodes of dominating $f_1$ and $f_2$ can easily be localized in time and in frequency simultaneously. Importantly, in the RE we observe intermittent short lasting moments of strong $f_2$ (lasting about 25-30 ms duration) indicative of central fixation while the FFT amplitudes of the two components are approximately equal. On the right side (LE), there is a continuous steady $f_2$ component indicating stable central fixation when working with a threshold of 0.4 or less. Should, however, the CWT threshold be placed at about 0.6, then the right eye would be passing, though intermittently, while the left eye would be failing to fixate on the target, and possible misalignment of the eyes would be suggested. Thresholds are set upon analyzing a large pool of clinically verified data.

The CWT can be performed in real time, and is expected to improve significantly detection sensitivity when testing uncooperative subjects.

According to some embodiments of the current invention, a mathematical method can be used for reliable detection of short lasting moments of eye fixation on a target using time-frequency distributions such as the Gabor Transform, Wigner-Ville Transform, Short-Time Fourier Transform, Choi-Williams distribution, and the Continuous Wavelet Transform. These transforms can be applied on the digitized signal obtained during retinal birefringence scanning, using a personal computer, digital signal processing system (DSP), an embedded controller, embedded microprocessor system, or any combination thereof. Using these transforms, one can detect characteristic frequencies, often of short duration, which yield information regarding the state of fixation of the eye.

In some embodiments, the state of fixation can be assessed for both eyes simultaneously, using separate signals from each eye, thus allowing for identification of short-lasting moments of proper alignment of the eyes, misalignment of the eyes with one another, or lack of attention to the target.

In some embodiments, noise caused by internal reflections in the apparatus, or external reflections coming from the test subject's face, lids, sclera, or cornea, can be discarded in the time-frequency plane, as long as the noise does not overlap in time and frequency simultaneously with the frequency and temporal location of the fixation event.

In some embodiments, a bull's eye photodetector consisting of concentric central and annular sensors to detect the goodness of focus of the light returning from the eye can be included, with such goodness of focus being judged at moments of short-lasting central fixation. In some embodiments, the fixation and goodness of focus can be analyzed simultaneously for both eyes during short-lasting periods of monocular or binocular fixation.

In some embodiments, the apparatus can be used for the detection of frequent and short-lasting losses of fixation, possibly indicative of nystagmus, attention-deficit-hyperactivity disorder (ADHD), autism, or other neuropsychologic disorders.

In some embodiments, analysis of occurrences of periods of binocular alignment versus occurrences of non-alignment can enable the differentiation between intermittent and constant misalignment of the eyes.

The analysis can be implemented using field programmable gate array (FPGA) logic, for example.

Conventional algorithms for detection of fixation, as just described, can be found in the following, each of which is incorporated herein by reference:

Bastiaans B, Gabor's expansion of a signal into. Gaussian elementary signals. Proc. IEEE 1980; 68:538-39.
Bastiaans B, A sampling theorem for the complex spectrogram, and Gabor's expansion of a signal in Gaussian elementary signals. Optical Engineering 1981; 20.
Chui C K. Wavelets: A tutorial in theory and applications.: Academic press., 1992.
Claasen T A C M, Mecklenbrauker W F G, The Wigner Distribution—A tool for time-frequency signal analysis. Phillips J. Res. 1980; 35:217-50; 76-300; 1067-72.
Cohen L, Wigner distribution for finite duration or band-limited signals and limited cases. IEEE Trans. Acoustics, Speech, Signal Processing 1987; 35:796-806.
Debnath L. Wavelets and Signal Processing. Boston-Basel-Berlin: Birkhauser, 2003.
Gramatikov B, Brinker J, Yi-chun S, Thakor N V, Wavelet analysis and time-frequency distributions of the body surface ECG before and after angioplasty. Comput Methods Programs Biomed 2000; 62:87-98.
Gramatikov B, Georgiev I, Wavelets as alternative to Short-Time Fourier transform in signal-averaged electrocardiography. Med Biol Eng Comput 1995; 33:482-7.
Gramatikov B, Thakor N. Wavelet analysis of coronary artery occlusion related changes in ECG. 15th Annual International Conference of the IEEE Engineering in Medicine and Biology Society. San Diego, Calif., 1993. p. 731.
Hogan J A, Lakey J D. Time-Frequency and Time-Scale Methods. Boston-Basel-Berlin: Birkhauser, 2005.
Holschneider M. Wavelets. An analysis tool. Oxford.: Clarendon Press., 1995.

Autoregressive Modeling

Time-frequency methods do allow localization of intermittent events in the time-frequency plane and allow acquisition and processing of very long epochs. Yet, these epochs are of finite duration, defined mostly by the capability of the electronics hardware. Important events can still be missed in the gaps between the signal epochs. These gaps, with intensive signal processing taking place in them, cannot be made shorter than several tens of milliseconds. Besides, the results are available only after acquiring the full epoch and analyzing all the data, which introduces a certain delay.

The goal is to achieve fast spectral analysis on very short time intervals, so that the procedure acquire process can be repeated continuously and indefinitely, thus avoiding any limitation on the duration of the epoch being analyzed. This allows detection of short-lasting events in the time-frequency plane, while avoiding any lengthy gaps that may potentially lead to missing moments of central fixation.

Parametric power spectrum estimation methods, such as Autoregressive (AR) methods, reduce the spectral loss problems. They can also be made faster than the Continuous Wavelet transform, which makes them suitable for real time applications. Autoregressive spectral estimation according to an embodiment of the current invention can be used to analyze short-lasting, non-stationary segments of the scanning signal. This method can provide an advantage over FFT's in that it uses shorter duration records and has better spectral resolution at that scale.

The AR methods (Akay 1994, Kay 1988, Kay and Marple 1981, Marple 1987, Proakis and Manolakis 1988) enable representation of a signal in a time interval by means of a set of parameters, the autoregressive coefficients:

$$x(n) = -\Sigma_{k=1}^{P} a(k)x(n-k) + \Sigma_{k=0}^{q} b(k)u(n-k) \quad (5)$$

in which x(n) is the output sequence of a causal filter that models the observed data, and u(n) is the input driving sequence. If all moving average parameters b(k) are zero, except b(0)=1, then $$x(n) = -\Sigma_{k=1}^{P} a(k)x(n-k) + u(n) \quad (6)$$

is strictly an autoregressive process of order p that allows for the calculation of the power spectrum density (PSD) in an unequivocal manner. For each signal segment x(n) being analyzed, once the AR parameters have been estimated, the power spectrum can be estimated as:

$$S_{AR}(f) = \frac{\sigma_p^2 \Delta t}{\left| 1 + \sum_{k=0}^{P} a_k \exp(-j2\pi f k \Delta t) \right|^2} \quad (7)$$

where f is the frequency, P is the order of the AR process, $a_k$ are the AR coefficients, $\sigma_p^2$ is the forward prediction error energy, and $\Delta t$ is the sampling period of the data sequence. The order determines the trade-off between resolution and estimate variance in AR spectra. The optimum order of the AR model is determined using the Akaike Information Criterion (Akaike 1974). To find the AR parameters $a_k$, different methods are used: Yule-Walker, Burg, Covariance, Modified covariance, and others. Having tested all of them, for our purpose, we find the Burg method (Burg 1975) to be suitable for some applications of the current invention. The Burg method minimizes the sum-squared of the forward and backward prediction errors and has minimal phase characteristics. In addition, we have found the Covariance method to be suitable for some applications of the current invention. The Covariance method utilizes the relationship between the forward linear prediction errors and the linear prediction coefficients. To determine whether the model actually fits the data, we computed the residuals between the true values and predicted values at each sample. A good AR model is indicated by the residuals being a white noise process. The whiteness of the residuals was tested using the cumulative periodogram method (Box and Jenkins 1976) and C statistic as a tool of determining whether or not a residual from an AR model fit contains significant second order correlations, thus being a measure of the quality of the model fit (Hinich 1997, Nikias and Raghuveer 1987).

Figure 6:
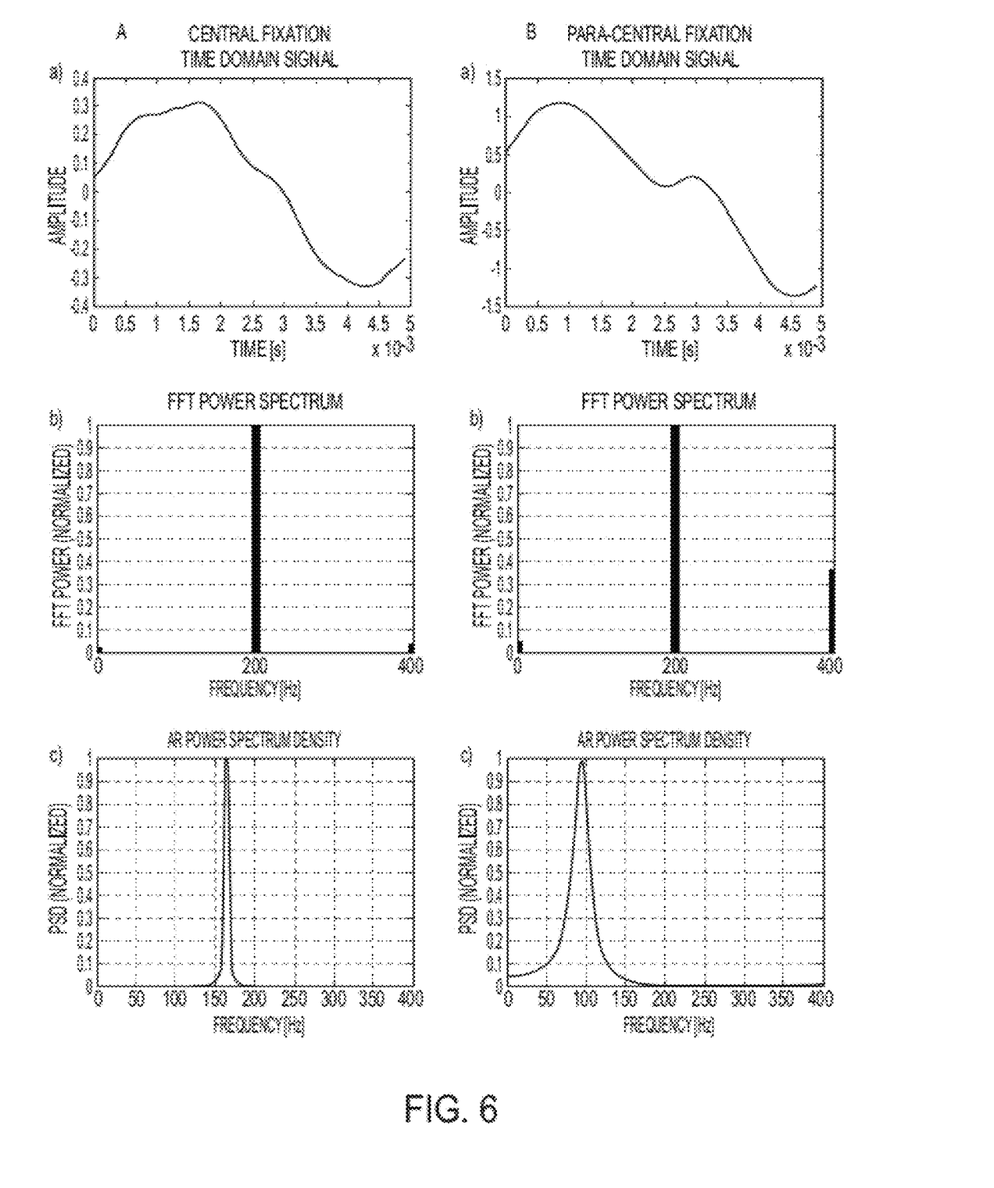
FIG. 6 illustrates some concepts of Auto-Regressive (AR)-based analysis during central fixation according to an embodiment of the current invention.

FIG. 6 illustrates an example of the AR-based analysis during central fixation (panel A, left column), and lack thereof (panel B, right column). The upper row (a) shows the time domain scan signal of duration T=5 ms (scanning frequency $f_s$=96 Hz, sampling rate of 10 kHz). The middle row (b) is the normalized FFT power of the same signal, having a spectral resolution of ~200 Hz (equal to 1/T). At such resolution, clearly, no frequencies between 0 Hz and 200 Hz can be identified. The lower row (c) shows the continuous AR power spectral densities (covariance method), capable of detecting intermediate frequencies. It can be seen how the peak of the dominant frequency shifts between 170 Hz (central fixation) and 96 Hz (paracentral fixation).

Figure 7:
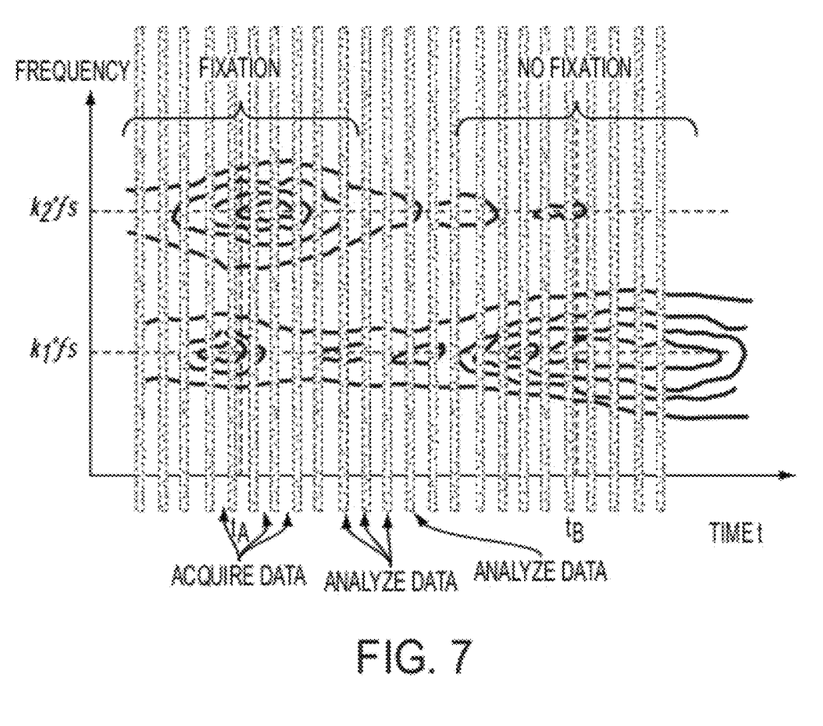
FIG. 7 illustrates some concepts of AR-based analysis according to an embodiment of the current invention.

Accordingly, an embodiment of the current invention combines fast AR spectral estimation of high frequency resolution, performed over short periods of time, with retinal birefringence scanning. It can enable detection of short-lasting moments of central fixation in the scan signal. AR can be superior to FFT because it allows frequency resolution that is not achievable with FFT on short time segments. With modern DSP technology, it can be performed fast, thus reducing signal gaps while increasing temporal resolution. In some embodiments, signal epochs of duration between 3-10 ms are acquired (white areas in FIG. 7), and immediately processed (shaded areas in FIG. 7), producing AR spectra of the type A-c) and B-c) (FIG. 6). On FIG. 7, for clarity, the signal is represented by its time-frequency distribution, rather than merely by the time-domain signal. The spectra are analyzed immediately, to detect the presence or absence of frequencies $f_1$, $f_2$, $f_3$, etc, indicative of the presence or absence of central fixation, after which a new signal epoch is acquired. In another embodiment, a dual-buffer ping-pong method can be used to analyze the data in a data buffer, while the twin buffer is being filled using direct memory access (DMA). Both options can offer continuous analysis in real time, not limited by any hardware. This can be implemented with the use of field programmable gate array (FPGA) logic, for example.

Conventional algorithms for detection of fixation, as just described, can be found in the following, each of which is incorporated herein by reference:

Akaike H, A new look at the statistical model identification. IEEE Trans. Automatic Control 1974; AC-19:716-23.

Akay M. Biomedical signal processing. San Diego, Calif.: Academic Press, Inc., 1994.

Box G E P, Jenkins G M. Time Series Analysis: Forecasting and Control. Oakland, Calif.: Holden-Day, 1976.

Burg J P. Maximum entropy spectral analysis. Dept. of Geophysics. Stanford, Calif.: Stanford Univ., 1975.

Hinich M J, Testing for dependence in the input to a linear time series model. Journal Nonparametric Statistics 1997.

Kay S M. Modern spectral estimation: theory and application. Englewood Cliffs, N.J.: Prentice Hall, 1988.

Kay S M, Marple S L, Spectrum analysis—A modern perspective. Proc. IEEE 1981; 69(11):1380-419.

Nikias C L, Raghuveer M R, Bispectrum estination: a digital signal processing framework. Proceedings of the IEEE 1987; 75:869-91.

Proakis J G, Manolakis D G. Introduction to digital signal processing. New York: Macmillan Publishing Company, 1988.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. An apparatus for detecting fixation of at least one eye of a subject on a target, comprising:
   an optical illumination system arranged to scan at least a portion of a retina of an eye of said subject with an illuminating beam of light;
   an optical detection system arranged to detect at least a portion of said illuminating beam of light after being reflected back from said retina of said subject's eye to provide a detection signal; and
   a signal processing system adapted to communicate with said optical detection system to receive said detection signal,
   wherein said illuminating beam of light is polarized light such that reflected portions of said illuminating beam are affected by birefringence of substructures of said retina of said subject's eye, wherein said detection signal has a first frequency signature when said subject's eye is fixed on said target and a second frequency signature when said subject's eye is not fixed on said target,
   wherein said signal processing system is configured to calculate at least one of a time-frequency distribution or an Auto-Regressive spectral estimation of said detection signal to provide a frequency distribution of said detection signal at a plurality of times for use in determining periods in which said subject's eye is fixed on said target based on said first and second frequency signatures, and
   wherein a time resolution of said at least one of a time-frequency distribution or an Auto-Regressive spectral estimation is smaller than 0.03 seconds and a frequency resolution of said time-frequency distribution is smaller than 5 Hz.

2. The apparatus according to claim 1, wherein said substructures of said portion of said retina of said subject's eye scanned comprise Henle fibers surrounding a fovea of said subject's eye.

3. The apparatus according to claim 1, wherein a time resolution of said at least one of a time-frequency distribution or an Auto-Regressive spectral estimation is sufficient to provide said frequency distribution for time intervals shorter than an average involuntary reflex time of human subjects.

4. The apparatus according to claim 1, wherein said signal processing system is configured to calculate said time-frequency distribution using at least one of a short time Fourier transform, a Continuous Wavelet Transform, a Wigner-Ville distribution, a Gabor Transform, a Choi-Williams distribution.

5. The apparatus according to claim 4, wherein said signal processing system is configured to calculate said time-frequency distribution using said Continuous Wavelet Transform.

6. The apparatus according to claim 1, wherein said signal processing system is configured to calculate said Auto-Regressive spectral estimation employing at least one of a Yule-Walker, Burg, Covariance, Modified covariance, Marple, least-square (LS) method, a Levinson-Durbin algorithm, a maximum likelihood estimation (MLE) method, Maximum Entropy (ME) method, or Prony method.

7. The apparatus according to claim 1, wherein said optical illumination system comprises a scanning assembly configured to scan said illuminating beam in a cyclical spatial pattern on said portion of said retina at a scanning frequency.

8. The apparatus according to claim 7, wherein said first frequency signature comprises at least one frequency component that is directly proportional to said scanning frequency by a first proportionality constant and said second frequency signature comprises at least one frequency component that is directly proportional to said scanning frequency by a second proportionality constant, wherein said first proportionality constant has a different value from a value of said second proportionality constant.

9. The apparatus according to claim 7, wherein said optical illumination system further comprises a polarization modulating assembly configured to modulate polarization of said illuminating beam at a polarization modulation frequency.

10. The apparatus according to claim 9, wherein said polarization modulation frequency is selected relative to said scanning frequency to provide at least partial cancellation of optical noise in said optical detection system.

11. The apparatus according to claim 1, wherein said an optical illumination system is adapted to scan at least a portion of a retina of the second eye of said subject with a second illuminating beam of light,
   wherein said optical detection system is arranged to detect at least a portion of said second illuminating beam of light after being reflected back from said retina of said subject's second eye to provide a second detection signal,
   wherein said signal processing system is further adapted to communicate with said optical detection system to receive said second detection signal,
   wherein said second illuminating beam of light is polarized light such that reflected portions of said second illuminating beam are affected by birefringence of substructures of said retina of said subject's second eye,
   wherein said second detection signal has a first frequency signature when said subject's second eye is fixed on said target and a second frequency signature when said subject's second eye is not fixed on said target, and
   wherein said signal processing system is configured to calculate at least one of a time-frequency distribution or an Auto-Regressive spectral estimation of said second detection signal to provide a frequency distribution of said second detection signal at a plurality of times for use in determining periods in which said subject's second eye is fixed on said target based on said first and second frequency signatures.

12. The apparatus according to claim 11, wherein the first mentioned detection signal and said second detection signal are obtained substantially simultaneously while in operation.

13. The apparatus according to claim 1, wherein said optical detection system further comprises a bull's eye photodetector comprising concentric central and annular sensors to detect a focus quality of said light after being reflected back from said retina of said subject's eye.

14. A method for detecting fixation of at least one eye of a subject on a target, comprising:
   scanning at least a portion of a retina of an eye of said subject with an illuminating beam of light;
   detecting at least a portion of said illuminating beam of light after being reflected back from said retina of said subject's eye to provide a detection signal; and
   processing said detection signal,
   wherein said illuminating beam of light is polarized light such that reflected portions of said illuminating beam are affected by birefringence of substructures of said retina of said subject's eye,
   wherein said detection signal has a first frequency signature when said subject's eye is fixed on said target and a second frequency signature when said subject's eye is not fixed on said target, wherein said processing said detection signal comprises calculating at least one of a time-frequency distribution or an Auto-Regressive spectral estimation of said detection signal to provide a frequency distribution of said detection signal at a plurality of times for use in determining periods in which said subject's eye is fixed on said target based on said first and second frequency signatures, and wherein a time resolution of said at least one of a time-frequency distribution or an Auto-Regressive spectral estimation is smaller than 0.03 seconds and a frequency resolution of said time-frequency distribution is smaller than 5 Hz.

\* \* \* \* \*